(12) United States Patent
Park et al.

(10) Patent No.: US 6,753,018 B2
(45) Date of Patent: Jun. 22, 2004

(54) METHOD FOR PROCESSING GINSENG AND PROCESSED GINSENG OBTAINED BY THE SAME

(75) Inventors: Seo-Young Park, Seoul (KR); Sool-Youn Cho, Seoul (KR); Il-Ho Park, Kyungg-do (KR); Yong-Jae Lee, Kyungg-do (KR); Man-Ki Park, Kyungg-do (KR); Jeong-Hill Park, Seoul (KR)

(73) Assignee: Ginseng Science Inc., Seoul (KR)

( * ) Notice: Subject to any disclaimer, the term of this patent is extended or adjusted under 35 U.S.C. 154(b) by 0 days.

(21) Appl. No.: 10/078,708

(22) Filed: Feb. 21, 2002

(65) Prior Publication Data

US 2003/0026858 A1 Feb. 6, 2003

(30) Foreign Application Priority Data

Jun. 25, 2001 (KR) ........................................ 2001-36236

(51) Int. Cl.⁷ ................................................ A61K 35/78
(52) U.S. Cl. ...................................................... 424/728
(58) Field of Search ......................................... 424/728

(56) References Cited

U.S. PATENT DOCUMENTS 5,776,460 A  *  7/1998  Kim et al.

FOREIGN PATENT DOCUMENTS

CN             1200892          * 12/1998

* cited by examiner

Primary Examiner—Christopher R. Tate
(74) Attorney, Agent, or Firm—Birch, Stewart, Kolasch & Birch, LLP

(57) ABSTRACT

Disclosed are a method for processing Panax spp., comprising the step of steaming Panax spp. under the oxygen-enriched atmosphere and a processed Panax spp. obtained by the method.

4 Claims, 1 Drawing Sheet

METHOD FOR PROCESSING GINSENG AND PROCESSED GINSENG OBTAINED BY THE SAME

TECHNICAL FIELD

The present invention relates to a method for processing ginseng and a processed ginseng obtained by the method. More specifically, the invention relates to a method for processing ginseng characterized by steaming ginseng under the oxygen-enriched atmosphere, which can enhance pharmacological effects of ginseng, and accelerate a browning reaction to reduce the processing time, and a processed ginseng obtained by the method.

BACKGROUND ART

Panax ginseng, one of *Panax spp.*, has been used as the best miraculous medicine in the Orient, such as China, Japan and the like including Korea, for thousands years. Ginseng has nutritious tonic, analgesic, sedative, stomachic and laxative effects. In addition, through modern scientific researches, ginseng has been discovered to have various pharmacological effects, for example, anticancer activity, immunosuppressive activity, therapeutic activity on exposure to radiation, improvement of memory, reduction of side effects from psychotropic drugs, anti-diabetic activity, etc.

Panax spp. practically used as health foods or medicines includes *P. ginseng, P. quinquefolia, P. notoginseng, P. japonica*, etc. Particularly, *P. quinquefolia*, so-called American ginseng, is used as a substitute for *P. ginseng* in Southeast Asia. Such Panax spp. shares a common ingredient, saponins, in a large quantity.

Ginseng is classified into fresh ginseng, white ginseng and red ginseng, according to its processing processes. Fresh ginseng is raw ginseng harvested in the field. White ginseng is obtained by drying fresh ginseng, and red ginseng is obtained by steaming fresh ginseng followed by drying the steamed ginseng. Particularly, red ginseng is known to have remarkably enhanced pharmacological effects, such as anti-oxidant, alcohol detoxifying, anti-thrombotic and anticancer activities, compared with fresh or white ginseng.

Red ginseng of high quality is red and has homogeneous color and good shape, and contains neither inner hole nor inner white factor. Red ginseng is divided into heaven ginseng, earth ginseng, and fine ginseng, according to its quality. Particularly, heaven ginseng of high quality is produced in a low yield during the processing process, and thus, is very expensive.

A steaming process is the most important process in the production of red ginseng. During the steaming process, unique ingredients of ginseng are formed and ginseng turns red due to a browning reaction. However, the steaming process for a long time or at a high temperature facilitates the browning reaction, but deteriorates the shape and quality of red ginseng to reduce the yield of high quality red ginseng.

In order to solve the above-described problems, it has been tried to improve the quality of ginseng by steaming it at a low temperature (Korean Patent Publication No. 92-5995). However, in such a case, reductions in the content of unique ingredients of red ginseng and in the browning reaction are not avoidable. Therefore, it has been required to develop a new processing method, which can improve quality of red ginseng while maintaining its pharmacological effects, and can simultaneously shorten the processing time.

DISCLOSURE OF THE INVENTION

The present inventors have performed extensive studies to reveal the reasons why ingredients and pharmacological effects of ginseng are changed during the production process of red ginseng. Unexpectedly, the inventors found that steaming under the atmosphere, where air is replaced by oxygen, accelerates the browning reaction, and strengthens pharmacological effects of red ginseng, and thus, completed the present invention.

Accordingly, an object of the present invention is to provide a method for processing ginseng characterized by steaming ginseng under the oxygen-enriched atmosphere, which can produce red ginseng having more enhanced pharmacological effects, and accelerate the browning reaction to reduce the processing time. Ultimately, the method of the present invention can increase the yield of high quality red ginseng.

Another object of the present invention is to provide a processed ginseng obtained by the method.

The present invention relates to a method for processing Panax spp., comprising the step of steaming Panax spp. under the oxygen-enriched atmosphere. In a preferable embodiment, the steaming process is carried out under the atmosphere containing oxygen of 50% or more.

In addition, the present invention relates to a processed Panax spp. obtained by the method.

Panax spp., as used herein, includes an undried or dried root of *P. ginseng, P. quinquefolia, P. notoginseng, P. japonica*, etc.

BEST MODE FOR CARRYING OUT THE INVENTION

Figure 1:
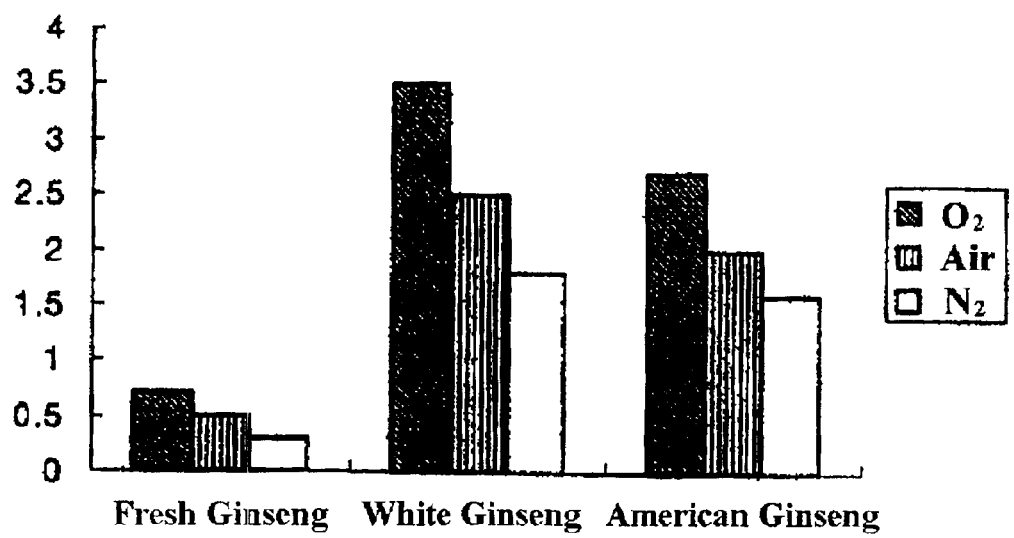
FIG. 1 is a graph showing absorbances of fresh ginseng, white ginseng and American ginseng, each of which was steamed under oxygen, air and nitrogen, respectively.
Figure 2:
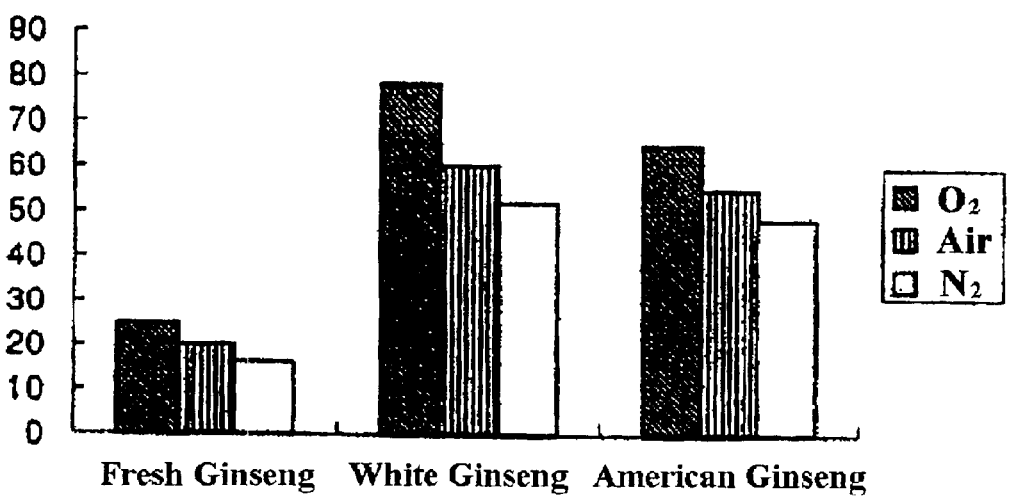
FIG. 2 is a graph showing anti-oxidant activities of fresh ginseng, white ginseng and American ginseng, each of which was steamed under oxygen, air and nitrogen, respectively.

This invention will be better understood from the following examples. However, one skilled in the art will readily appreciate the specific materials and results described are merely illustrative of, and are not intended to, nor should be intended to, limit the invention as described more fully in the claims, which follows thereafter.

EXAMPLE 1

As a steamer for steaming ginseng, 9 autoclaves (DAC-811, Dae Il Machine Company, Korea) were prepared and equipped with valves to be tightly closed. As experimental groups treated with oxygen, fresh ginseng, white ginseng and a dried root of *P. quinquefolia* (American ginseng), each of which was 50 g, were introduced into 3 autoclaves, respectively. Then, vacuum pumps were connected to the valves and the inner air was eliminated under reduced pressure. After closing the valves, oxygen tanks were connected thereto and oxygen was filled into the autoclaves. The above deaerating and filling processes were repeated twice to make the inside of the autoclaves under 1 atm of oxygen.

As a nitrogen-treated control (1) and an air-treated control (2), nitrogen and air, instead of oxygen, were filled into the autoclaves, respectively, according to the above method.

Subsequently, the valves of the autoclaves were closed and the temperature was raised to 100° C. Fresh ginseng, white ginseng and American ginseng were steamed for 3 hours, respectively. To the each steamed ginseng was added 500 ml of distilled water, and the mixture was extracted while heating to 100° C. for 3 hours. Distilled water was added to the obtained extract to make a final volume of 500 ml.

Experiment 1: Measurement of the Browning Level

Absorbance of each extract was measured at 400 nm using ultra violet/visible spectrophotometer (Beckrnann DU650). The measured absorbances are shown in the following Table 1.

TABLE 1

Absorbance of extract from Panax spp. steamed under oxygen, air and nitrogen

|  | Fresh ginseng | | | White ginseng | | | American ginseng | | |
| --- | --- | --- | --- | --- | --- | --- | --- | --- | --- |
| Treatment | $O_2$ | Air | $N_2$ | $O_2$ | Air | $N_2$ | $O_2$ | Air | $N_2$ |
| Absorbance | 0.7 | 0.5 | 0.3 | 3.5 | 2.5 | 1.8 | 2.7 | 2.0 | 1.6 |

As shown in the above table, fresh ginseng, white ginseng and American ginseng steamed under oxygen showed the highest absorbance, which indicated that the browning reaction was most efficiently preceded. Therefore, the method of the present invention was confirmed to accelerate the browning reaction.

Experiment 2: Measurement of Anti-oxidant Activity

Since elimination of DPPH (1,1-diphenyl-2-piczyl-hydrazyl) free radicals changes the color of DPPH solution [Blois, Nature, vol. 181, p 1199 (1959)], anti-oxidant activity was measured according to the elimination method of DPPH free radicals, as follows.

As sample solutions, the extracts were diluted with 60% methanol to adjust the concentration of ginseng to 20 mg/ml. DPPH of 4 mg was dissolved in 100 ml of 60% methanol to prepare a DPPH solution. The following solutions were allowed to stand at 37° C. for 30 minutes, respectively: a mixed solution of the DPPH solution (750 µl) and the sample solution (200 µl) (sample); a mixed solution of 60% methanol (750 µl) and the sample solution (200 µl) (blank), and a mixed solution of the DPPH solution (750 µl) and 60% methanol (200 µl) (control). Absorbance of each solution was measured at 515 nm.

Anti-oxidant activity (elimination activity of free radicals) was calculated from the following formula:

Anti-oxidant activity (%)=(C−S)/(C−B)×100

C: Absorbance of the control
B: Absorbance of the blank
S: Absorbance of the sample The above procedure was applied to fresh ginseng, white ginseng and American ginseng, respectively. The anti-oxidant activities are shown in the following Table 2.

TABLE 2

Anti-oxidant activity of ginseng steamed under oxygen, air and nitrogen

|  | Fresh ginseng | | | White ginseng | | | American ginseng | | |
| --- | --- | --- | --- | --- | --- | --- | --- | --- | --- |
| Treatment | $O_2$ | Air | $N_2$ | $O_2$ | Air | $N_2$ | $O_2$ | Air | $N_2$ |
| Absorbance | 25 | 20 | 16 | 78 | 60 | 52 | 65 | 55 | 48 |

As shown in the above table, fresh ginseng, white ginseng and American ginseng steamed under oxygen showed the highest anti-oxidant activity. Therefore, the method of the present invention was confirmed to enhance the anti-oxidant activity of ginseng.

INDUSTRIAL APPLICABILITY

As described above, the processing method of ginseng of the present invention can enhance its pharmacological effects, and accelerate its browning reaction to shorten the processing time.

What is claimed is:

1. A method for preparing a red ginseng, comprising the step of steaming Panax spp. under an oxygen enriched atmosphere containing 50% or more of oxygen for a time sufficient to prepare the red ginseng; and thereafter recovering the red ginseng.

2. The method according to claim 1, wherein the Panax spp. is a dried or undried root of *Panax ginseng, Panax quinquefolia, Panax notoginseng* or *Panax japonica*.

3. A steamed The method according to claim 1, wherein the Panax spp. is steamed at 100° C.

4. The method according to claim 1, wherein the Panax spp. is heated in an autoclave under at least 1 atm, of oxygen for at least about 3 hours during the steaming step.

* * * * *